United States Patent
Levorse, Jr. et al.

(10) Patent No.: US 9,181,514 B2
(45) Date of Patent: Nov. 10, 2015

(54) OCTAHYDRO-BENZOFURANS AND THEIR USES IN PERFUME COMPOSITIONS

(71) Applicant: International Flavors & Fragrances Inc., New York, NY (US)

(72) Inventors: Anthony T. Levorse, Jr., Westfield, NJ (US); Nicole L. Giffin, Hazlet, NJ (US); Robert P. Belko, Monroe, NJ (US); Michael G. Monteleone, Hazlet, NJ (US)

(73) Assignee: International Flavors & Fragrances, Inc., New York, NY (US)

( * ) Notice: Subject to any disclaimer, the term of this patent is extended or adjusted under 35 U.S.C. 154(b) by 0 days.

(21) Appl. No.: 14/305,616

(22) Filed: Jun. 16, 2014

(65) Prior Publication Data
US 2014/0296120 A1    Oct. 2, 2014

Related U.S. Application Data

(62) Division of application No. PCT/US2013/022073, filed on Jan. 18, 2013.

(60) Provisional application No. 61/587,716, filed on Jan. 18, 2012, provisional application No. 61/587,720, filed on Jan. 18, 2012, provisional application No. 61/587,722, filed on Jan. 18, 2012, provisional application No. 61/587,726, filed on Jan. 18, 2012, provisional application No. 61/587,728, filed on Jan. 18, 2012, provisional application No. 61/587,740, filed on Jan. 18, 2012, provisional application No. 61/587,742, filed on Jan. 18, 2012, provisional application No. 61/587,747, filed on Jan. 18, 2012, provisional application No. 61/587,749, filed on Jan. 18, 2012, provisional application No. 61/587,753, filed on Jan. 18, 2012, provisional application No. 61/587,754, filed on Jan. 18, 2012, provisional application No. 61/587,755, filed on Jan. 18, 2012, provisional application No. 61/587,759, filed on Jan. 18, 2012, provisional application No. 61/587,757, filed on Jan. 18, 2012.

(51) Int. Cl.
*C11D 3/50* (2006.01)
*C11B 9/00* (2006.01)

(52) U.S. Cl.
CPC ............... *C11B 9/0076* (2013.01); *C11D 3/50* (2013.01)

(58) Field of Classification Search
CPC ...................................................... C07D 307/79
USPC ............................. 549/462; 510/103; 512/13
See application file for complete search history.

(56) References Cited

PUBLICATIONS

M. Yokota et al., Chemical Communications 2003, issue 3, pp. 422-423 (abstract).*
E. Piers et al., Canadian Journal of Chemistry 1969, vol. 47, issue 5, pp. 831-840 (abstract).*
A. Srikirshna et al., Tetrahedron Letters 1995, vol. 36, issue 7, pp. 1127-1128 (abstract).*

* cited by examiner

*Primary Examiner* — John Hardee
(74) *Attorney, Agent, or Firm* — XuFan Tseng; Martin Zhang; Elizabeth M. Quirk

(57) ABSTRACT

The present invention is directed to novel fragrance compounds and their unexpected advantageous use in improving, enhancing or modifying a fragrance formulation through the addition of an olfactory acceptable amount of the compounds, wherein the compounds are represented by the following formula:

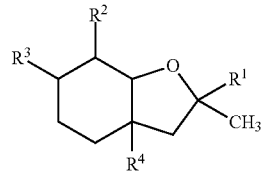

wherein $R^1$, $R^2$ and $R^3$ are independently selected from the group consisting of hydrogen and methyl; and $R^4$ is a $C_1$-$C_3$ alkyl group.

20 Claims, No Drawings

OCTAHYDRO-BENZOFURANS AND THEIR USES IN PERFUME COMPOSITIONS

STATUS OF RELATED APPLICATIONS

This application is a divisional of PCT/US2013/022073, filed on Jan. 18, 2013, which claims benefit of priority from U.S. provisional applications 61/587,716; 61/587,720; 61/587,722; 61/587,726; 61/587,728; 61/587,740; 61/587,742; 61/587,747; 61/587,749; 61/587,753; 61/587,754; 61/587,755; 61/587,757 and 61/587,759 filed Jan. 18, 2012, the contents hereby incorporated by references as if set forth in their entirety.

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how small differences in chemical structures can result in unexpected and significant differences in odor, notes and characteristics of molecules. These variations allow perfumers and other persons to apply new compounds in creating new fragrances.

SUMMARY OF THE INVENTION

The present invention provides novel chemicals and their unexpected advantageous use in enhancing, improving or modifying the fragrance of perfumes, colognes, toilet waters, fabric care products, personal products and the like.

More specifically, the present invention is directed to novel octahydro-benzofurans that exhibit unexpected strong fragrance effect, particularly herbal, sweet, camphor, woody, fresh, green, spice, flora, eucalyptus, and slight piney notes, and a method of improving, enhancing or modifying a fragrance formulation through the addition of an olfactory acceptable amount of octahydro-benzofurans represented by Formula I set forth below:

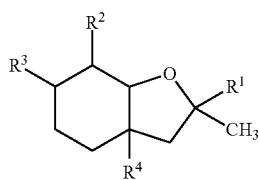

Formula I wherein $R^1$, $R^2$ and $R^3$ are independently selected from the group consisting of hydrogen and methyl; and
$R^4$ is a $C_1$-$C_3$ alkyl group.

These and other embodiments of the present invention will be apparent by reading the following specification.

DETAILED DESCRIPTION OF THE INVENTION

It is known to those with the skill in the art that Formula I as defined above provides the following novel compounds:

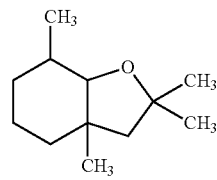

Formula II

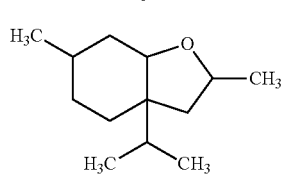

Formula III

Those with the skill in the art will recognize that:
Formula II represents 2,2,3a,7-tetramethyl-octahydro-benzofuran; and
Formula III represents 3a-isopropyl-2,6-dimethyl-octahydro-benzofuran.

The compounds of the present invention were prepared with cyclohexanones according to the following reaction scheme, the details of which are specified in the Examples. Materials and catalysts were purchased from Sigma-Aldrich Chemical Company unless noted otherwise.

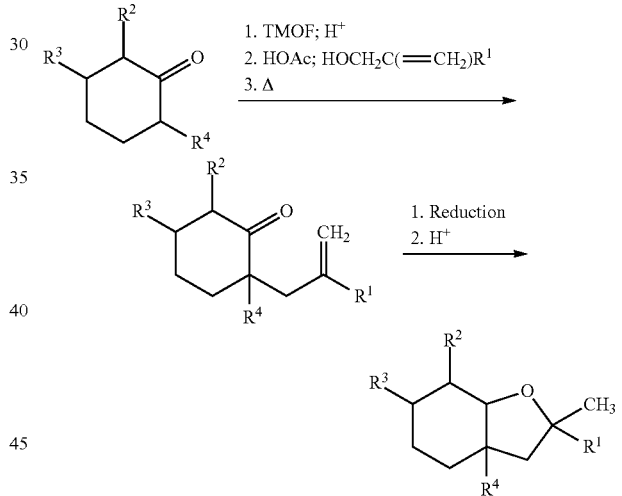

wherein $R^1$, $R^2$, $R^3$ and $R^4$ are defined as above;
TMOF represents trimethyl orthoformate;
HOAc represents acetic acid; and
Δ represents heating.

Those with skill in the art will recognize that the compounds of the present invention may have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly silica gel chromatography and solid phase microextraction, referred to as SPME.

2,2,3a,7-Tetramethyl-octahydro-benzofuran has been surprisingly found to possess unexpected fragrance effect such as, for example, herbal, sweet, camphor, woody, fresh, and green notes.

3a-Isopropyl-2,6-dimethyl-octahydro-benzofuran has been surprisingly found to possess strong and unexpected fragrance effect such as, for example, cedar wood, green, spice, flora, eucalyptus, and slight piney notes.

The use of the compounds of the present invention is widely applicable in current perfumery products, including the preparation of perfumes and colognes, the perfuming of personal care products such as soaps, shower gels, and hair care products, fabric care products as well as air fresheners and cosmetic preparations. These compounds can also be used to perfume cleaning agents, such as, but not limited to detergents, dishwashing materials, scrubbing compositions, window cleaners and the like. In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like. A list of suitable fragrances is provided in U.S. Pat. No. 4,534,891, the contents of which are incorporated by reference as if set forth in its entirety. Another source of suitable fragrances is found in Perfumes, Cosmetics and Soaps, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The term "improving" in the phrase "improving, enhancing or modifying a fragrance formulation" means raising the fragrance formulation to a more desirable character. The term "enhancing" means making the fragrance formulation greater in effectiveness or providing the fragrance formulation with an improved character. The term "modifying" means providing the fragrance formulation with a change in character.

The terms "fragrance formulation", "fragrance composition", and "perfume composition" mean the same and refer to a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance formulation of the present invention is a fragrance formulation comprising a compound of the present invention.

The term "fragrance product" means a consumer product that adds a fragrance or masks a malodor. Fragrance products may include, for example, perfumes, colognes, personal care products such as soaps, shower gels, and hair care products, fabric products, air fresheners, cosmetic preparations, and perfume cleaning agents such as detergents, dishwashing materials, scrubbing compositions, and window cleaners. The fragrance product of the present invention is a consumer product that contains a compound of the present invention.

Olfactory acceptable amount is understood to mean the amount of a compound in a fragrance formulation, wherein the compound will contribute its individual olfactory characteristics. However, the olfactory effect of the fragrance formulation will be the sum of effect of each of the fragrance ingredients. Thus, the compounds of the present invention can be used to improve or enhance the aroma characteristics of the fragrance formulation, or by modifying the olfactory reaction contributed by other ingredients in the formulation. The olfactory acceptable amount may vary depending on many factors including other ingredients, their relative amounts and the olfactory effect that is desired.

The amount of the compounds of the present invention employed in a fragrance formulation varies from about 0.005 to about 50 weight percent, preferably from 0.5 to about 25 weight percent, and more preferably from about 1 to about 10 weight percent. Those with skill in the art will be able to employ the desired amount to provide desired fragrance effect and intensity. In addition to the compounds of the present invention, other materials can also be used in conjunction with the fragrance formulation. Well known materials such as surfactants, emulsifiers, polymers to encapsulate the fragrance can also be employed without departing from the scope of the present invention.

When used in a fragrance formulation, the compounds of the present invention provide unexpected strong herbal, sweet, camphor, woody, fresh, green, spice, flora, eucalyptus, and slight piney characteristics and make the fragrance formulation more desirable and noticeable. The odor qualities found in the compounds of the present invention assist in beautifying and enhancing the finished accord and improve the performance of other materials in the fragrance formulation.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, L is understood to be liter, mL is understood to be milliliter, mol is understood to be mole, Kg is understood to be kilogram, g is understood to be gram and mol is understood to be mole. IFF as used in the examples is understood to mean International Flavors & Fragrances Inc., New York, N.Y., USA.

EXAMPLE I

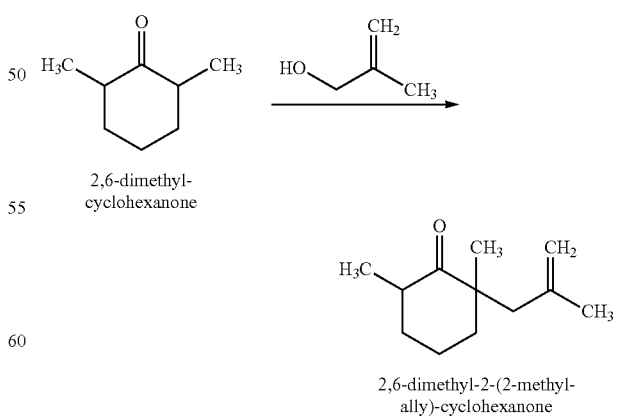

2,6-dimethyl-cyclohexanone 2,6-dimethyl-2-(2-methyl-ally)-cyclohexanone

Preparation of 2,6-dimethyl-2-(2-methyl-allyl)-cyclohexanone: 2,6-Dimethyl-cyclohexanone (1 kg, 4 mol), trimethyl orthoformate (TMOF, 880 g), and methanol (800 mL) were charged to a 5 L reaction flask. HCl was added quickly. Reaction exothermed and the temperature increased from 14° C. to 20° C. The reaction mixture was heated to 60° C. and aged for 7 hours. When the reaction was about 75% complete, the reaction mixture was quenched with NaOCH$_3$ (25%, 25 g), heated to 90° C., and applied to a Dean-Stark trap. The reaction mixture was then cooled to room temperature followed by sequential addition of methallyl alcohol (1.25 Kg, 8.5 moles), HOAc (50 g), and methane sulfonic acid (MSA, 10 g). The resulting mixture was heated to 110° C., applied to a Bidwell-Sterling trap, and aged for 4 hours until gas chromatograph analysis indicated that the reaction was 95% completed. The reaction mixture was then cooled and washed with saturated sodium carbonate solution (3 L) to provide the crude product 2,6-dimethyl-2-(2-methyl-allyl)-cyclohexanone.

EXAMPLE II

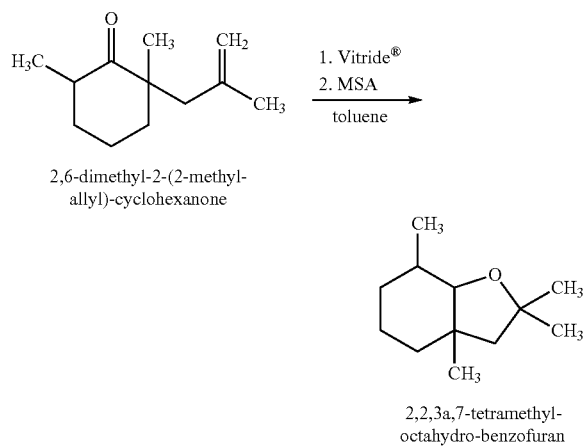

Preparation of 2,2,3a,7-tetramethyl-octahydro-benzofuran (Formula II): A 3 L reaction flask was charged with Vitride® (325 g, 0.9 mol) and toluene (500 mL), heated to 100° C., fed with 2,6-dimethyl-2-(2-methyl-allyl)-cyclohexanone (200 g, 1.1 mol, obtained in EXAMPLE I) for over 2 hours, and aged for another 2 hours. After the reaction completed, the reaction mixture was cooled to room temperature, quenched with IPA (100 mL). NaOH (50%, 300 g) and water (200 mL) were then added, heated to 80° C., and aged for another hour. The reaction mixture was cooled to room temperature and more water (200 mL) was added. Layers were split to dispose the aqueous waste. The organic layer was charged back to the flask. Toluene (300 mL) was added and water was removed with a Dean-Stark trap through azeotrope. The resuling mixture was cooled to 50° C. MSA (28 g, 0.3 mol) was added and the reaction mixture was heated to reflux. The consumption of the starting material was indicated after 3 hours. The resulting mixture was then cooled to room temperature and washed with saturated sodium carbonate solution (1 L) followed by brine (1 L). Distillation and fractionation provided the product 2,2,3a,7-tetramethyl-octahydro-benzofuran (125 g) in 63% yield.

$^1$H NMR (CDCl$_3$, 500 MHz): 3.17 (d, J=5.7 Hz, 1H), 1.26 (s, 3H), 1.20 (s, 3H), 1.05 (s, 3H), 0.93 (d, J=7.2 Hz, 3H), 0.80-1.78 (m, 9H)

2,2,3a,7-Tetramethyl-octahydro-benzofuran was described as having herbal, sweet, camphor, woody, fresh and green notes with low strength.

EXAMPLE III

Preparation of 3a-isopropyl-2,6-dimethyl-octahydro-benzofuran (Formula III): Menthone (500 g), trimethylorthoformate (377 g) and methanol (400 mL) were charged to a 3 L reaction flask. In one portion, hydrochlorioc acid (3 g) was added and the mixture exothermed from 22° C. to 40° C. The reaction mixture was aged 6 hours and quenched with sodium methoxide solution (35 g). Low boiling materials were removed while the reaction mixture was heated to 90° C. Allyl alcohol (404 g) and acetic acid (195 g) were added and the reaction mixture was heated to 160° C. The reaction mixture was held at 160° C. for 3 hours, cooled to 25° C., and washed with brine (500 mL). The crude product was distilled to provide a mixture of allyl menthone isomers.

Red-Al® (397 g) was charged to a 2 L reaction flask and heated to 55° C. Allyl menthone isomers (248 g, obtained in above) were fed into the flask and the reaction was allowed to exotherm to 70° C. The reaction mixture was aged for 8 hours and quenched with isopropanol (100 mL) followed by aqueous sodium hydroxide solution (50%, 307 g). The resulting organic layer was washed with brine (500 mL). The crude alcohol was distilled to provide a mixture of allyl menthol isomers.

Allyl menthol isomers (200 g, obtained in above), toluene (500 mL), and methanesulfonic acid (MSA, 5 g) were charged to 1 L reaction flask. The reaction mixture was heated to 80° C., aged for 8 hours, then cooled to 22° C., and washed with aqueous sodium carbonate solution (10%, 300 mL). The resulting crude mixture was purified by distillation to afford 3a-isopropyl-2,6-dimethyl-octahydro-benzofuran in (130g) 65% yield.

$^1$H NMR (CDCl$_3$, 500 MHz): 3.40-4.25 (m, 2H), 0.75-2.17 (m, 10H), 1.28 (d, J=6.3 Hz, 3H), 0.96 (d, J=6.6 Hz, 3H), 0.89 (d, J=6.9 Hz, 6H)

3a-Isopropyl-2,6-dimethyl-octahydro-benzofuran was described as having cedar wood, green, spice, flora, eucalyptus, and slight piney notes.

What is claimed is:

1. A compound:

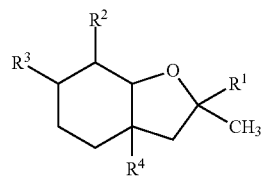

wherein $R^1$, $R^2$ and $R^3$ are independently selected from the group consisting of hydrogen and methyl; and $R^4$ is a $C_1$-$C_3$ alkyl group.

2. The compound of claim 1, wherein the compound is 2,2,3a,7-tetramethyl-octahydro-benzofuran.

3. The compound of claim 1, wherein the compound is 3a-isopropyl-2,6-dimethyl-octahydro-benzofuran.

4. A fragrance formulation containing an olfactory acceptable amount of a compound:

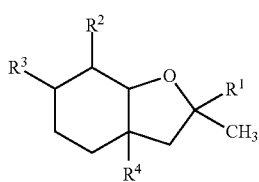

wherein R¹, R² and R³ are independently selected from the group consisting of hydrogen and methyl; and
R⁴ is a $C_1$-$C_3$ alkyl group.

5. The fragrance formulation of claim 4, wherein in the compound is 2,2,3a,7-tetramethyl-octahydro-benzofuran.

6. The fragrance formulation of claim 4, wherein the compound is 3a-isopropyl-2,6-dimethyl-octahydro-benzofuran.

7. The fragrance formulation of claim 4 further comprising a product selected from the group consisting of a perfume, a cologne, toilet water, a cosmetic product, a personal care product, a fabric care product, a cleaning product and an air freshener.

8. The fragrance formulation of claim 7, wherein the cleaning product is selected from the group consisting of a detergent, a dishwashing composition, a scrubbing compound and a window cleaner.

9. The fragrance formulation of claim 4, wherein the olfactory acceptable amount is from about 0.005 to about 50 weight percent of the fragrance formulation.

10. The fragrance formulation of claim 4, wherein the olfactory acceptable amount is from about 0.5 to about 25 weight percent of the fragrance formulation.

11. The fragrance formulation of claim 4, wherein the olfactory acceptable amount is from about 1 to about 10 weight percent of the fragrance formulation.

12. A method of improving, enhancing or modifying a fragrance formulation through the addition of an olfactory acceptable amount of a compound of formula:

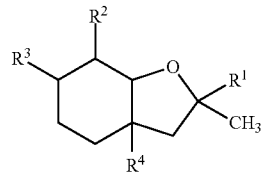

wherein R¹, R² and R³ are independently selected from the group consisting of hydrogen and methyl; and
R⁴ is a $C_1$-$C_3$ alkyl group.

13. The method of claim 12, wherein in the compound is 2,2,3a,7-tetramethyl-octahydro-benzofuran.

14. The method of claim 12, wherein the compound is 3a-isopropyl-2,6-dimethyl-octahydro-benzofuran.

15. The method of claim 12, wherein the olfactory acceptable amount is from about 0.005 to about 50 weight percent of the fragrance formulation.

16. The method of claim 12, wherein the olfactory acceptable amount is from about 0.5 to about 25 weight percent of the fragrance formulation.

17. The method of claim 12, wherein the olfactory acceptable amount is from about 1 to about 10 weight percent of the fragrance formulation.

18. A fragrance product comprising the compound of claim 1.

19. The fragrance product of claim 18, wherein in the compound is 2,2,3a,7-tetramethyl-octahydro-benzofuran.

20. The fragrance product of claim 19, wherein the compound is 3a-isopropyl-2,6-dimethyl-octahydro-benzofuran.

* * * * *